(12) United States Patent
Vortman et al.

(10) Patent No.: US 11,272,904 B2
(45) Date of Patent: Mar. 15, 2022

(54) ULTRASOUND FOCUSING USING A CROSS-POINT SWITCH MATRIX

(71) Applicants: Kobi Vortman, Haifa (IL); Shuki Vitek, Haifa (IL); Yoav Levy, Hinanit (IL)

(72) Inventors: Kobi Vortman, Haifa (IL); Shuki Vitek, Haifa (IL); Yoav Levy, Hinanit (IL)

(73) Assignee: INSIGHTEC, LTD., Tirat Carmel (IL)

( * ) Notice: Subject to any disclaimer, the term of this patent is extended or adjusted under 35 U.S.C. 154(b) by 1259 days.

(21) Appl. No.: 15/627,922

(22) Filed: Jun. 20, 2017

(65) Prior Publication Data

US 2018/0360420 A1    Dec. 20, 2018

(51) Int. Cl.
*A61B 8/00* (2006.01)
*A61B 5/01* (2006.01)
(Continued)

(52) U.S. Cl.
CPC .............. *A61B 8/4488* (2013.01); *A61B 5/01* (2013.01); *A61B 5/055* (2013.01); *A61B 8/5215* (2013.01);
(Continued)

(58) Field of Classification Search
CPC ....... A61B 8/4488; A61B 8/5215; A61B 5/01; A61B 5/055; A61N 7/02; B06B 1/0292; B06B 1/0622; G01S 7/52022
(Continued)

(56) References Cited

U.S. PATENT DOCUMENTS 6,135,963 A   10/2000  Haider
7,950,397 B2 *  5/2011  Thapliyal ........... A61B 18/1492
                                                128/898
(Continued)

FOREIGN PATENT DOCUMENTS

EP         2540246 A1    1/2013

OTHER PUBLICATIONS

Extended European Search Report for European Application No. 18178538.7 dated Oct. 24, 2018 9 pages.

*Primary Examiner* — Amelie R Davis
*Assistant Examiner* — Marjan Saboktakin
(74) *Attorney, Agent, or Firm* — Morgan, Lewis & Bockius LLP

(57) ABSTRACT

A system for delivering ultrasound energy to an internal anatomical target includes an ultrasound transducer having multiple transducer elements collectively operable as a phased array; multiple driver circuits, each being connected to at least one of the transducer elements; multiple phase circuits; a switch matrix selectably coupling the driver circuits to the phase circuits; and a controller configured for (i) receiving as input a target average intensity level and/or an energy level energy to be applied to the target and/or a temperature level in target, (ii) identifying multiple sets of the transducer elements, each of the sets corresponding to multiple transducer elements for shaping and/or focusing, as a phased array, ultrasound energy at the target across tissue intervening between the target and the ultrasound transducer, and (iii) sequentially operating the transducer-element sets to apply and maintain the target average energy level at the target. In various embodiments, the controller operates each of the transducer element sets in accordance with a pulse-width modulation pattern having a duty cycle selected to achieve the target average intensity level, energy (Continued)

level, and/or temperature level at the target in accordance with a time constant of the target tissue.

33 Claims, 10 Drawing Sheets

(51) Int. Cl.
| | |
|---|---|
| *A61B 5/055* | (2006.01) |
| *G01S 7/52* | (2006.01) |
| *A61B 8/08* | (2006.01) |
| *A61B 17/22* | (2006.01) |
| *A61B 17/00* | (2006.01) |
| *A61B 18/00* | (2006.01) |
| *A61N 7/02* | (2006.01) |
| *B06B 1/02* | (2006.01) |
| *B06B 1/06* | (2006.01) |
| *A61N 7/00* | (2006.01) |
| *A61B 90/00* | (2016.01) |

(52) U.S. Cl.
CPC .............. *A61N 7/02* (2013.01); *B06B 1/0292* (2013.01); *B06B 1/0622* (2013.01); *G01S 7/52022* (2013.01); *A61B 17/22004* (2013.01); *A61B 2017/00084* (2013.01); *A61B 2017/00154* (2013.01); *A61B 2017/22008* (2013.01); *A61B 2017/22014* (2013.01); *A61B 2017/22027* (2013.01); *A61B 2018/0075* (2013.01); *A61B 2018/00708* (2013.01); *A61B 2018/00726* (2013.01); *A61B 2018/00791* (2013.01); *A61B 2090/374* (2016.02); *A61N 2007/0039* (2013.01); *A61N 2007/0052* (2013.01); *A61N 2007/0078* (2013.01); *A61N 2007/0095* (2013.01); *A61N 2007/027* (2013.01); *G01S 7/52085* (2013.01)

(58) Field of Classification Search
USPC ........................................................ 600/411
See application file for complete search history.

(56) References Cited

U.S. PATENT DOCUMENTS

| | | | |
|---|---|---|---|
| 2004/0236253 A1* | 11/2004 | Vortman | G10K 11/346 601/2 |
| 2009/0230823 A1* | 9/2009 | Kushculey | A61B 8/4494 310/366 |
| 2014/0324085 A1* | 10/2014 | Thapliyal | A61B 8/12 606/169 |
| 2015/0080705 A1* | 3/2015 | Partanen | A61B 5/7264 600/411 |
| 2015/0105701 A1* | 4/2015 | Mayer | A61B 18/1206 601/3 |

* cited by examiner

ULTRASOUND FOCUSING USING A CROSS-POINT SWITCH MATRIX

FIELD OF THE INVENTION

The field of the invention relates generally to ultrasound systems and, more particularly, to systems and methods for facilitating ultrasound focusing using a cross-point switch matrix.

BACKGROUND

Focused ultrasound (i.e., acoustic waves having a frequency greater than about 20 kiloHertz) can be used to image internal body tissues or, at high intensity, to generate thermal ablation energy to treat tissue such as tumors or disrupt vasculature to deliver drugs. By way of illustration, FIG. 1 is a simplified schematic representation of an exemplary focused ultrasound system 100 used to generate and deliver a focused acoustic energy beam 102 to a targeted tissue 104 in a patient 106. The system 100 employs an ultrasound transducer 108 that is geometrically shaped and physically positioned relative to the patient 106 in order to focus the ultrasonic energy beam 102 at a three-dimensional focal zone located within the targeted tissue 104. The system can shape the ultrasonic energy in various ways, producing, for example, a point focus, a line focus, a ring-shaped focus, or multiple foci simultaneously. The transducer 108 may be substantially rigid, semi-rigid, or substantially flexible, and can be made from a variety of materials, such as ceramics, plastics, polymers, metals, and alloys. The transducer 108 can be manufactured as a single unit, or, alternatively, be assembled from a plurality of components. While the illustrated transducer 108 has a "spherical cap" shape, a variety of other geometric shapes and configurations may be employed to deliver a focused acoustic beam, including other non-planar as well as planar (or linear) configurations. The dimensions of the transducer may vary, depending on the application, between millimeters and tens of centimeters.

The transducer 108 may include a large number of transducer elements 110, arranged in a one-, two- or three-dimensional array or other regular manner, or in an uncoordinated fashion. These elements 110 convert electronic drive signals into mechanical motion and, as a result, into acoustic waves. They may be made, for example, of piezoelectric ceramics or piezo-composite materials, and may be mounted in silicone rubber or another material suitable for damping the mechanical coupling between the elements 110. The transducer elements 110 are connected via electronic drive signal channels 112 to a control module 114, which drives the individual transducer elements 110 so that they collectively produce a focused ultrasonic beam. More specifically, the control module 114 may include a beamformer 116 that sets the relative amplitudes and phases of the drive signals in channels 112. In conventional focused ultrasound systems containing n transducer elements, the beamformer 116 typically contains n amplifiers 118 and n phase control circuits 120, each pair driving one of the transducer elements 110. The beamformer 116 receives a radio frequency (RF) input signal, typically in the range from 0.1 MHz to 5 MHz, from frequency generator 122. The input signal may be split into n channels for the n amplifiers and phase circuits 118, 120 of the beamformer 116. Thus, in typical conventional systems, the radio frequency generator 122 and the beamformer 116 are configured to drive the individual elements 110 of the transducer 108 at the same frequency, but at different phases and different amplitudes, such that the transducer elements 110 collectively form a "phased array."

The acoustic waves transmitted from the transducer elements 110 form the acoustic energy beam 102. Typically, the transducer elements are driven so that the waves converge at a focal zone in the targeted tissue 104. Within the focal zone, the wave energy of the beam 102 is (at least partially) absorbed by the tissue, thereby generating heat and raising the temperature of the tissue to a point where the cells are denatured and/or ablated. To effectively treat the target tissue, the acoustic energy beam 102 must be precisely focused to the target location to avoid damage to healthy tissue surrounding the target region. As the acoustic energy beam 102 passes through the intervening tissue, beam scattering, absorption, reflection, and/or refraction may occur due to tissue inhomogeneity; this may result in beam aberrations, which may distort the focus and reduce the intensity, thus affecting treatment efficiency. Accordingly, it is desired to adjust parameters (e.g., phase shifts and/or amplitudes) of the drive signals associated with the transducer elements so as to compensate for the acoustic aberrations and thereby improve focusing properties at the target region.

The acoustic beam 102 may be directed to focus at a number of different focal zones. Adjusting the drive signals so as to focus the acoustic energy at various desired locations is a process known as "electronic steering" of the beam 102. The amplification (or attenuation factors) a and the phase shifts φ imposed by the beamformer 116 and used to steer the beam are computed in a controller 124. By independently adjusting the relative phases and/or amplitudes of the drive signals in the channels 112 associated with the transducer elements 110, the location and properties of the focused acoustic beam can be controlled.

To independently adjust the phases and/or amplitudes of the drive signals, however, complex circuitry may be required, as each of the channels 112 may require a dedicated amplifier 118 and a phase control circuit 120 (e.g., n amplifiers 118 and n phase control circuits 120 may be required when there are n channels 112). In addition, as the number of the transducer elements 110 increases, the ability to independently drive the elements with various phase shifts and various amplitudes becomes concomitantly less practical for complexity and cost reasons.

Accordingly, there is a need for accommodating large numbers of transducer elements in a transducer array without the burden of employing individual amplifiers and phase-control circuits associated with the transducer element, but also without sacrificing the beam focusing and steering capabilities needed in specific clinical applications.

SUMMARY

Embodiments of the present invention provide an ultrasound system that allows elements in a transducer array to be operated individually or in a grouped manner without the need for excessive supporting circuitry. In various embodiments, the ultrasound system includes a beamformer for generating drive signals for the transducer array and multiple phase-control circuits for imparting various phase shifts to the drive signals. The phase-control circuits may each generate a phase shift different from one another and the generated phase shifts may cover a range of 0 to 2π. In some embodiments, each transducer element (or each group of transducer elements if the elements are grouped) is associated with a drive channel that may be connected to one of the phase-control circuits via a cross-point switch matrix. The cross-point switch matrix includes multiple switches; each switch may couple a drive channel to a phase-control circuit.

During an ultrasound procedure, a controller in the ultrasound system may determine phase shifts (which may be discretized) that cause the transducer elements (or groups of transducer elements) to collectively produce a focused ultrasonic beam at a target region. The controller or the beamformer may operate the cross-point switch matrix to couple the transducer elements (or groups of transducer elements) to the phase-control circuits having the determined discrete phase shifts; this activates the transducer elements (or groups of transducer elements) to thereby transmit acoustic beams having the determined phase shifts. To achieve a treatment goal (e.g., a target average intensity level, a target average energy level and/or a target temperature level at the target region), in various embodiments, pulse-width modulation (PWM) is implemented to facilitate operation of the switches in the cross-point matrix, thereby adjusting durations (i.e., duty cycles) of the elements' activation time. The duty cycles positively correlate to energy levels delivered to the target region—a higher duty cycle corresponds to larger energy, because the power is on for most of the time. Thus, PWM allows the energy levels of acoustic beams to be effectively adjusted without changing the amplitudes of the drive signals; this advantageously reduces system complexity and expense.

The duty cycles of the transducer elements (or groups of transducer elements) may be varied based on a mechanical time constant and/or a thermal time constant (hereafter, collectively, a "time constant") of the targeted tissue. In one embodiment, to ensure that the target tissue responses are not significantly impacted by deactivation of the transducer elements (i.e., during an "off time" of the drive signal), the off time of the drive signals is smaller than the time constant of the target tissue.

As described above, as an acoustic beam passes through the tissue located between the transducer elements and target region, beam aberration may occur due to inhomogeneity of the intervening tissue. This may reduce the intensity level at the target region, thereby affecting the treatment efficiency. To compensate for this effect, in one embodiment, the duty cycles of the transducer elements (or groups of transducer elements) are adjusted based on their beam energy levels detected at the target region (a detected energy level at the target region that is too low requires an increase in the duty cycle as one of the mitigation steps).

Beam aberration resulting from the intervening tissue may also distort the focal profile at the target region and/or generate an inhomogeneous temperature distribution, including hot spots, at the target or non-target region. (The term "hot spot" is herein used to connote a concentrated region of ultrasound energy that raises the temperature of the tissue in which it occurs to a clinically unacceptable level.) In one embodiment, the transducer elements (or groups of transducer elements) are sequentially operated in round-robin fashion. This way, the elements (or groups of elements) having distorted acoustic beams are deactivated for a time interval, and adverse effects resulting from the beam aberration may be reduced.

In some embodiments, an imager (e.g., an MRI apparatus) and/or an acoustic cavitation detector is employed to monitor a treatment parameter (e.g., a temperature or a level of cavitation) in the target and/or non-target region; the monitored parameter is then provided as feedback for adjusting operation of the transducer elements so as to achieve the treatment goals as reflected/measured by the monitoring. Again, the operation of the transducer elements may be adjusted via adjusting the duty cycles thereof.

Accordingly, in one aspect, the invention pertains to a system for delivering ultrasound energy to an internal anatomical target. In various embodiments, the system includes an ultrasound transducer having multiple transducer elements collectively operable as a phased array; multiple driver circuits, each of the driver circuits being connected to one or more of the transducer elements; multiple phase circuits; a switch matrix (e.g., a crosspoint switch matrix) selectably coupling the driver circuits with the phase circuits; and a controller configured for (i) receiving as input a target average intensity level to be applied to the target, an energy level to be applied to the target and/or a temperature level in target, (ii) identifying multiple sets of the transducer elements, each of the sets corresponding to multiple transducer elements for focusing and/or shaping, as a phased array, ultrasound energy at the target across tissue intervening between the target and the ultrasound transducer, and (iii) sequentially operating the transducer-element sets to apply and maintain the target average energy level at the target. In one implementation, the controller operates each of the transducer element sets in accordance with a pulse-width modulation pattern having a duty cycle selected to achieve the target average intensity level, energy level and/or temperature level at the target in accordance with an estimated time constant of the target tissue.

The target average intensity level may be a spatial or temporal average intensity level. The driver circuits may be greater in number than the phase circuits, and the controller may selectively connect each of the phase circuits to multiple driver circuits. In addition, the phase circuits may deliver signals having a discrete number of fixed phase shifts, and the controller may be further configured to apply one of the fixed phase shifts to one of the transducer elements or to one of the transducer element sets. In one embodiment, the controller is further configured to adjust the fixed phase shifts based on the shaping of the ultrasound energy and/or a location of the target.

In various embodiments, the system includes a magnetic resonance (MR) unit for monitoring a temperature of the target, and the controller is configured to adjust the duty cycle in response to the monitored temperature. In addition, the controller may be further configured to responsively operate the switch matrix to energize or ground selected ones of the transducer elements of each of the sets so as to reduce temperature inhomogeneities in an ultrasound beam path zone and/or the target detected by the MR monitoring. In some embodiments, the MR unit is further configured to monitor a location and profile of the focus, and the controller is configured to responsively operate the switch matrix to energize or ground the selected ones of the transducer elements of each of the sets so as to reduce profile distortion of the focus.

The system may further include a cavitation detector for detecting cavitation at the focus; the controller is configured to responsively operate the switch matrix to energize or ground selected ones of the transducer elements of each of the sets so as to reduce or increase peak pressure at the focus in the presence of detected cavitation. In some embodiments, the cavitation detector is coupled to the controller, and the controller is further configured to (i) responsively operate the switch matrix to energize or ground selected ones of the transducer elements of each of the sets and (ii) facilitate pulse width modulation of signals driving the multiple sets of the transducer elements so as to achieve a cavitation effect in a predefined range. In one implementation, one or more transducer elements are shared between two or more sets of the transducer elements. In addition, the controller may be further configured to simultaneously operate more than one set of the transducer elements.

In various embodiments, the switch matrix is configured to couple the driver circuits to the phase circuits, an electrical ground, and/or a voltage source having a fixed voltage. In addition, the controller may be further configured to operate each of the transducer element sets to produce a point focus, a line focus, a ring-shaped focus or multiple foci at the target. The controller may be further configured to operate the transducer elements to generate a focus at the target. Further, the controller may be configured to sequentially operate the transducer-element sets in round-robin fashion.

In another aspect, the invention relates to a method for delivering ultrasound energy to an internal anatomical target utilizing an ultrasound transducer having multiple transducer elements collectively operable as a phased array, multiple driver circuits each connected to one or more transducer elements, multiple phase circuits, and a switch matrix (e.g., a crosspoint switch matrix) selectably coupling the driver circuits with the phase circuits. In various embodiments, the method includes receiving as input a target average intensity level to be applied to the target, an energy level to be applied to the target, and/or a temperature level in target; identifying multiple sets of transducer elements, each of the sets corresponding to multiple transducer elements for shaping and/or focusing, as a phased array, ultrasound energy at the target across tissue intervening between the target and the ultrasound transducer; and sequentially operating the transducer-element sets to apply and maintain the target average energy level at the target. In one implementation, the controller operates each of the transducer element sets in accordance with a pulse-width modulation pattern having a duty cycle selected to achieve the target average intensity level, energy level and/or temperature level at the target in accordance with a time constant of the target tissue.

The method may further include monitoring a temperature of the target and adjusting the duty cycle in response to the monitored temperature. In one embodiment, the method includes monitoring temperature inhomogeneities in an ultrasound beam path zone and/or the target and responsively operating the switch matrix to energize or ground selected ones of the transducer elements of each of the sets so as to reduce the temperature inhomogeneities. The method may further include monitoring a location and profile of the focus, and responsively operating the switch matrix to energize or ground the selected ones of the transducer elements of each of the sets so as to reduce profile distortion of the focus.

In addition, the phase circuits may deliver signals having a discrete number of fixed phase shifts; the method further includes applying one of the fixed phase shifts to one of the transducer elements or one of the transducer element sets. In one embodiment, the method includes adjusting the fixed phase shifts applied to the one of the transducer elements or the one of the transducer element sets based on the shaping of the ultrasound energy and/or a location of the target. The driver circuits may be greater in number than the phase circuits; the method may further include selectively connecting each of the phase circuits to multiple driver circuits.

The method may further include detecting cavitation at the focus and responsively operating the switch matrix to energize or ground selected ones of the transducer elements of each of the sets so as to reduce or increase peak pressure at the focus in the presence of detected cavitation. In some embodiments, the method includes detecting cavitation at the focus; responsively operating the switch matrix to energize or ground the selected ones of the transducer elements of each of the sets; and facilitating pulse width modulation of signals driving the sets of the transducer elements so as to achieve a cavitation effect in a predefined range. In one implementation, the method includes simultaneously operating one or more sets of the transducer elements.

In various embodiments, the method further includes operating each of the transducer element sets for producing a point focus, a line focus, a ring-shaped focus or multiple foci at the target. In addition, the method may include sequentially operating the transducer-element sets in round-robin fashion. The target average intensity level may be a spatial or temporal average intensity level.

As used herein, the term "substantially" means±10%, and in some embodiments, ±5%. In addition, the term "element" means either an individual transducer in an array or an independently drivable portion of a single transducer, and the terms "beam," "energy beam," or "acoustic energy beam" refer generally to the sum of the waves emitted by the various transmitting elements of a focused ultrasound system. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Phased-array ultrasound transducers in accordance with various embodiments of the invention typically include a large number (e.g., hundreds and up to thousands) of individual transducer elements whose linear dimensions in general are no greater than the wavelength of the acoustic waves generated during operation. Using small transducer elements results in increased steerability of the acoustic beam in three-dimensions—i.e., steering of both the depth of focus and the lateral focus position, over a large volume. For example, with transducer element dimensions of no more than half a wavelength, the steering angle (i.e., the maximum angle with respect to the normal of the transducer surface that can be achieved) in each direction is $\pm \pi/2$, which facilitates covering a complete hemisphere. In certain embodiments, the transducer elements are of uniform size and shape and are evenly arranged (e.g., in a tiled fashion) so as to form an isotropic array. In other embodiments, the transducer elements are of various sizes and/or shapes and may be arranged in any suitable manner, depending on the clinical application and/or the shape and location of the patient's body to which the transducer elements are proximately placed.

Figure 1:
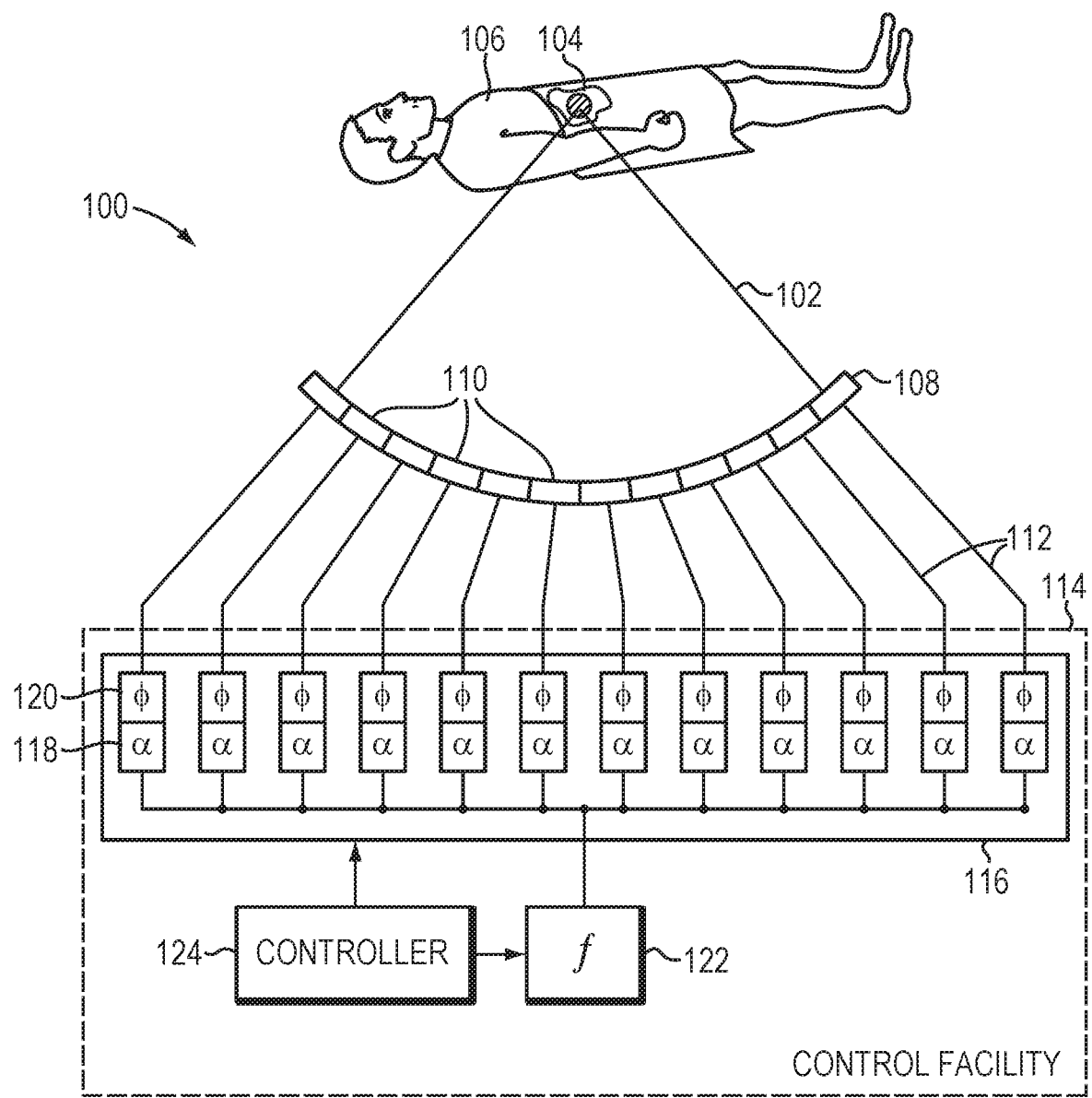
FIG. 1 illustrates a focused ultrasound system described in the prior art.

As depicted in FIG. 1, in conventional ultrasound systems, each element 110 of the transducer array 108 is associated with one electronic drive signal channel 112; the beamformer 116 in the control facility 114 sets the relative amplitudes and phases of the drive signals in the channels 112 so as to drive the individual transducer elements 110 with corresponding settings, thereby collectively producing a focused ultrasonic beam. To control both the amplitude and phase of the drive signal in a single channel, however, requires an additional layer of electronic circuitry at the channel level; this increases the design burden and cost. To keep complexity and cost low, in various embodiments of the present invention, the relative phases of the drive signals are adjusted by the beamformer 116, whereas the amplitudes of the drive signals are fixed at one or more desired values during an ultrasound procedure as further described below. In addition, the controller 124 sets and adjusts relative duty cycles of the drive signals of the elements 110; this effectively controls energy levels of acoustic beams produced by the drive signals. For example, a duty cycle of 80% delivers a larger amount of thermal energy to the target region compared to a duty cycle of 30%. Accordingly, various embodiments of the present invention effectively adjust the intensity levels or energy level of the acoustic beams by varying the duty cycles of the transducer elements. This obviates the need to implement individual amplifiers 118 and corresponding supporting circuits for adjusting the amplitudes of the transducer drive signals.

In various embodiments, circuitry associated with the beamformer 116 is simplified by limiting the phase shifts available to the elements 110 to a number of discrete values. For example, there may be eight values of the phase shifts—$\varphi_1, \varphi_2, \varphi_3, \ldots \varphi_8$—available, and each element may receive one of the eight phase shifts.

Figure 2:
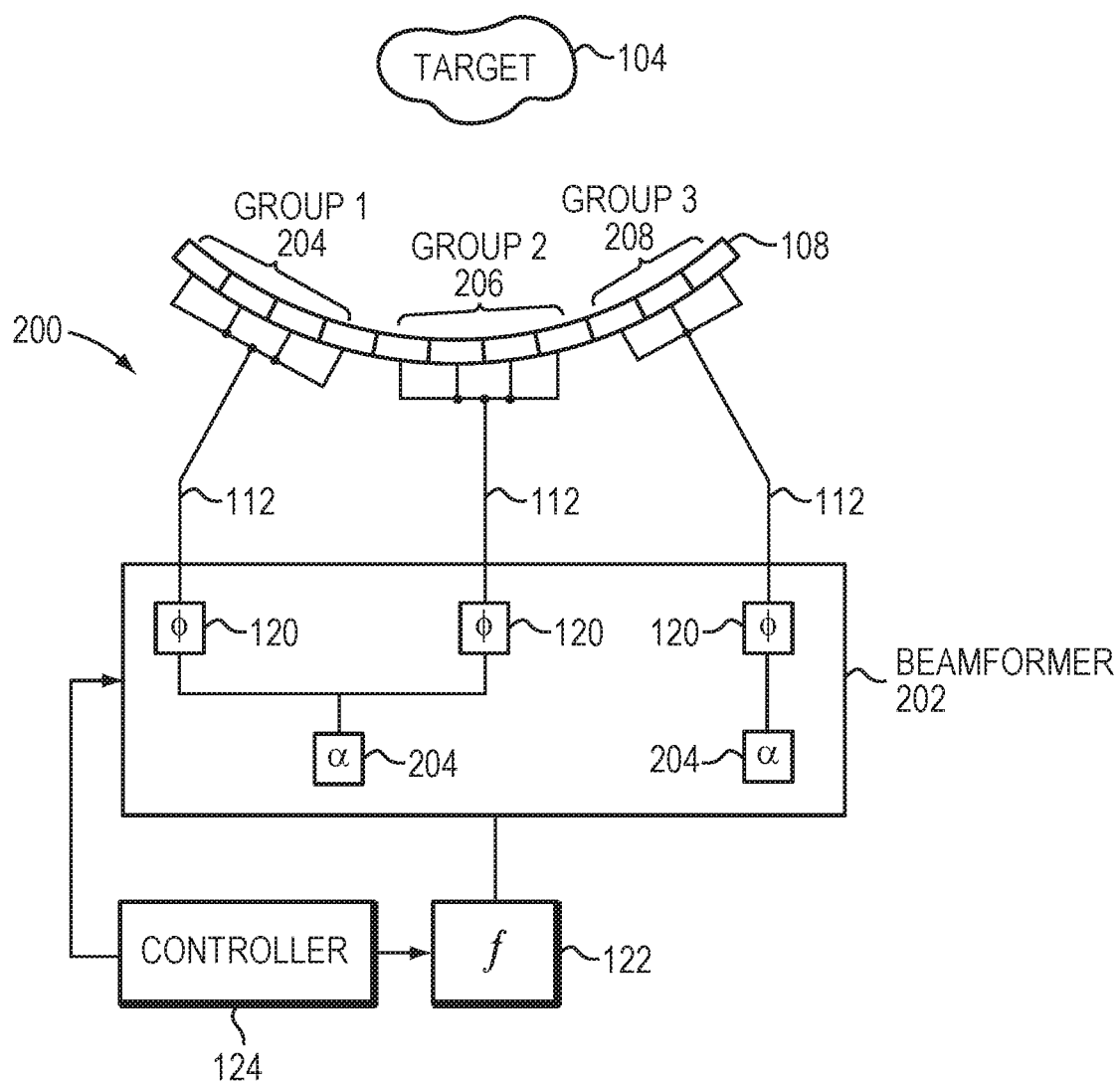
FIG. 2 schematically depicts an exemplary focused ultrasound system in accordance with various embodiments.

In addition, the transducer elements may be grouped, and elements within each group may be wired together so as to receive a drive signal from a single channel 112. As a consequence, the number of channels may be significantly smaller than the number of transducer elements. Each group may comprise a one- or two-dimensional array (i.e., a row or a matrix) of transducer elements 108; different groups may or may not share one or more transducer elements 108. The elements 110 within each group may form a single contiguous area of the transducer surface, or include multiple non-contiguous surface portions. In various embodiments, the groups of transducer elements 110 are separately controllable, i.e., they are each capable of emitting ultrasound waves with frequencies and/or phases that are independent of the frequencies and/or phases of the other groups. An exemplary implementation of such an ultrasound focusing system is conceptually illustrated in FIG. 2. In the depicted system 200, each group of the transducer elements 110 is connected to a phase-control circuit 120 via a drive signal channel 112. Because the number of drive signal channels 112 is smaller than the number of transducer elements 110, the complexity of the beamformer 202 is reduced (compared with that of a beamformer in a conventional system in which the phase of every element is separately controllable).

In various embodiments, the driver channels 112 of two or more groups 204, 206 share a common amplifier 204 to further reduce the system complexity; the transducer elements in the groups 204, 204 are driven with the same amplitude. In one embodiment, the ultrasound system 200 includes one amplifier only; thus, all groups of transducer elements are driven with the same amplitude of signals. The groups 204, 206, 208 of the transducer elements may be selectively activated and deactivated, one or more at a time, to transmit ultrasound to the target region as further described below; the frequencies, phases and/or duty cycles of the drive signals associated with the group 204, 206, 208 may be adjusted during ultrasound operation to achieve a treatment goal at the target region 104.

Acoustic beams transmitted from the transducer elements 100 (or groups of the transducer elements) may traverse intervening tissue located between the transducer array 108 and target region 104 prior to generating a focal zone at the target region 104. Inhomogeneity of the intervening tissue may decrease the intensity of the acoustic energy at the focal zone, distort the focal profile, and may even move the location of the focal zone. Specifically, because the speed of sound differs in different types of tissue, as portions of a beam of acoustic energy travel along different paths having different tissue types towards the focal zone, they may experience different speeds of sound, which may shift the relative phases of acoustic energy transmitted from respective transducer elements. This phase shifting may decrease the constructive interference of the acoustic energy at the focal zone, which may reduce the effectiveness of the treatment, or may even move the focal zone in an unpredictable manner.

Tissue inhomogeneity may also cause refraction of acoustic energy at the boundaries of tissue regions having different speeds of sound. Refraction may decrease constructive interference, and hence, the intensity of the acoustic energy at the focal zone, particularly when the acoustic energy passes through bone. Thus, inhomogeneous tissue structures may generate beam absorption, aberrations and refractions, which may distort the focus and reduce the intensity, thus affecting treatment efficiency.

Figure 3:
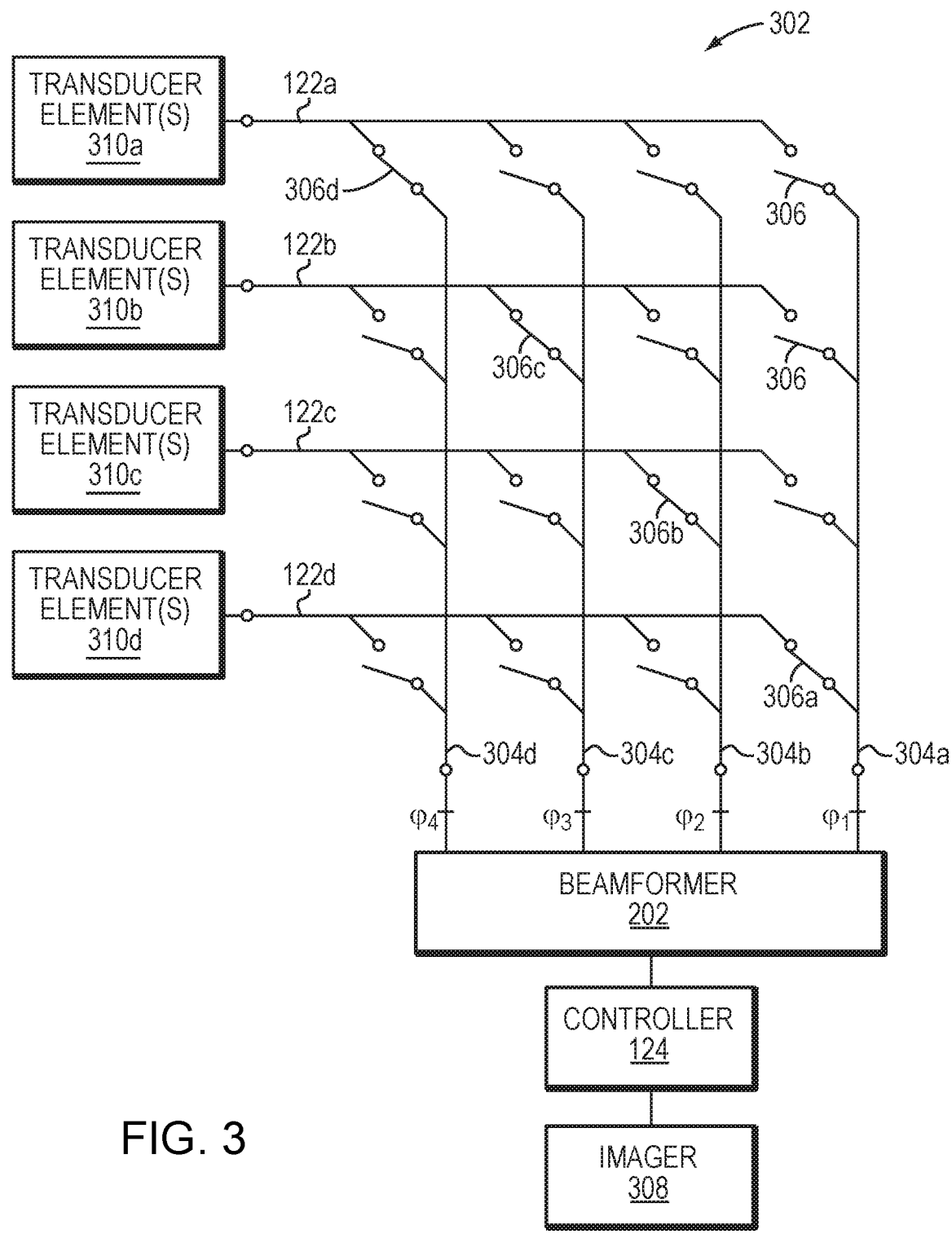
FIG. 3 illustrates a cross-point switch matrix for coupling transducer elements to a beamformer in accordance with various embodiments.

The acoustic aberrations caused by the inhomogeneous intervening tissue may be accounted for by adjusting the phase shift of each transducer element (or each group of transducer elements). Referring to FIG. 3, in various embodiments, a cross-point switch matrix 302 is implemented in series between the beamformer 202 and the transducer elements 110. The cross-point switch matrix 302 includes multiple phase-control lines 304 connecting to phase-control circuits of the beamformer 202 and multiple electronic switches 306 that may selectively couple and decouple drive channels 112 from the phase-control lines 304. The switches 306 may be, for example, mechanical switches and/or electrical switches (e.g., transistors). Each switch 306, upon activation, electrically couples a phase-control line 304 to a drive channel 112 associated with one (or more groups) of the transducer elements 110. The beamformer 202 may impart different phase shifts to the drive signals in different phase-control lines 304. For example, the beamformer 202 may generate drive signals having phase shifts $\varphi_1$-$\varphi_4$ in the phase-control lines 304a-304d, respectively. In some embodiments, the drive signals in some of the phase-control lines 304 have the same phase shift.

In some embodiments, the drive channels 112 are greater in number than the phase-control lines 304. Accordingly, during the ultrasound procedure, at least some transducer elements are not coupled to the phase-control lines 304; these elements 110 may be grounded or coupled to a voltage source having fixed voltages via the drive channels 112. Using a smaller number of phase-control lines 304 may advantageously reduce the circuitry complexity and expense. But this comes with a tradeoff, reducing the ability to precisely control the focusing properties at the target region; the lower the number of discrete phases or delay values is, the bigger will be the phase difference between the phase-control lines. This, in turn, limits the beamformer's capability to precisely control the phase shift of each acoustic beam transmitted from the transducer elements. Consequently, the ability to improve focusing properties is limited.

Prior to or during ultrasound operation, an imager 308 may be utilized to determine tissue information such as the location of the target tissue and anatomical characteristics of the target tissue and/or tissue surrounding the target. The imager 308 may include a magnetic resonance imaging (MRI) device, a computer tomography (CT) device, a positron emission tomography (PET) device, a single-photon emission computed tomography (SPECT) device, or an ultrasonography device. Based on the information acquired by the imager 308, the controller 124 may determine phase shifts for some or all elements 110 (or for each group of transducer elements 110) which, when applied, cause the emitted ultrasound beams to collectively form a constructive focal zone at the target region 104. The determined phase shifts are then communicated to the beamformer 202, and based thereon, the beamformer 202 selectively couples the phase-control lines 304 having the determined phase shifts to the corresponding transducer elements 110 (or groups of transducer elements) via the switches 306. For example, groups 310a-310d of the transducer elements in FIG. 3 may be driven with phase shifts of $\varphi_1$-$\varphi_4$, respectively, so as to create a focus at the target region 104. Upon receiving the determined phase shifts from the controller 124, the beamformer 202 may close the switches 306a-306d so as to couple the phase-control lines 304a-304d to drive channels 112a-112d, respectively. As a result, the transducer elements 310a-310d are driven by drive signals having the predetermined phase shifts of $\varphi_1$-$\varphi_4$, respectively. Accordingly, the acoustic energy from the transducer elements can be focused at various desired locations by selectively coupling the drive channels 112 to various phase-control lines 304 having different phase shifts, thereby providing electronic steering.

In various embodiments, to effectively treat tissue in the target region 104, a treatment plan, including, e.g., a target average intensity level, a target average energy level and/or a target temperature level associated with the target region 104, is determined prior to or during treatment based on anatomical characteristics of the target tissue acquired using the imager 308. As explained above, however, inhomogeneity of the intervening tissue located between the transducer array 108 and target region 104 may distort the acoustic beams, thereby decreasing the intensity of the acoustic energy reaching the focal zone and/or creating undesired hot spots on the beam paths or at the target region. It is thus desirable to adjust operating parameters (e.g., duty cycles) of the transducer elements 110 to compensate for effects resulting from the beam distortions so as to achieve the treatment plan. In one embodiment, the energy of the acoustic beam transmitted from each individual transducer element (or each group of transducer elements) is controlled via adjusting a duty cycle of its drive signal using pulse-width modulation (PWM). Because the duty cycles of the drive signals can be simply manipulated by activating and deactivating the switches 306 in the cross-point matrix 302, this embodiment advantageously allows the controller 124 to effectively control the energy levels of the acoustic beams while avoiding implementing complex amplitude-control circuitry.

Figure 4A:
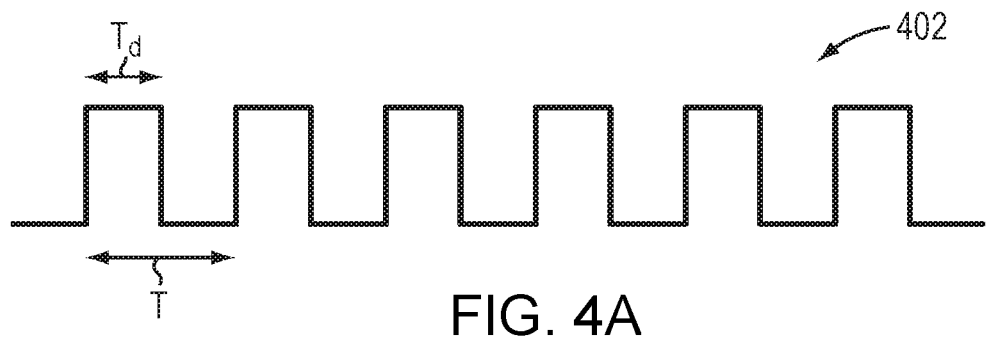
FIGS. 4A-C illustrate exemplary drive signals driving transducer elements in accordance with various embodiments.
Figure 4B:
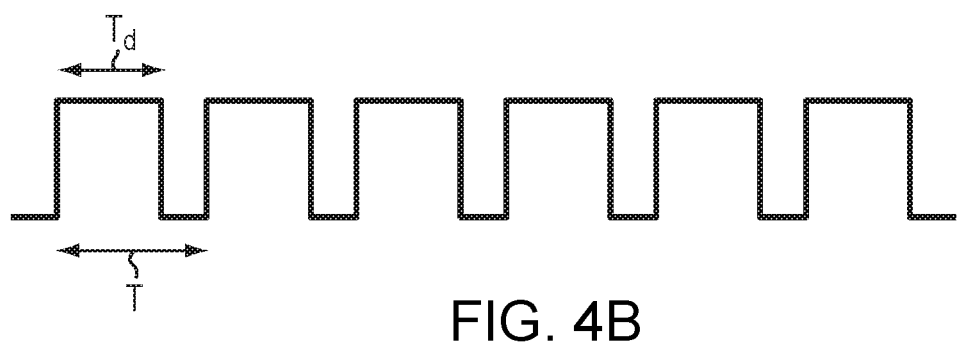
Figure 4C:
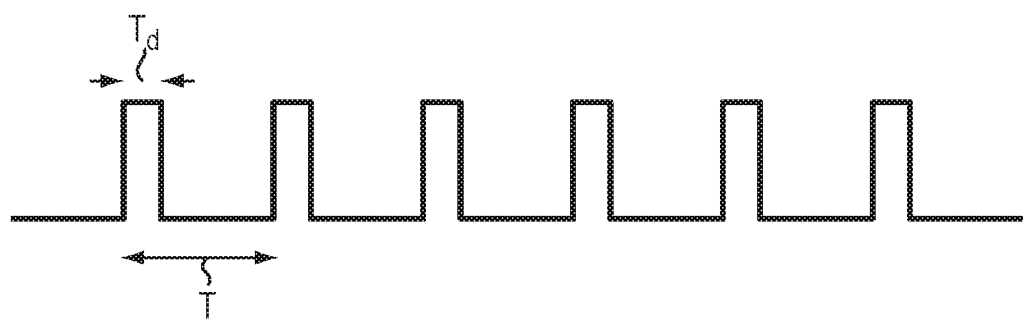

FIG. 4A illustrates an exemplary drive signal 402 driving a transducer element (or a group of the transducer elements) in accordance with various embodiments of the present invention. The ratio of the duration of the element's activation time, $T_d$, to the regular interval (i.e., the period of time), T, provides a duty cycle of the drive signal 402 that can determine the acoustic energy transmitted to the target region—a low duty cycle corresponds to low energy, because the power is off for most of the time. Duty cycle is typically expressed in percent, with 100% being fully on and 0% being fully off. Thus, by varying the duty cycle of the drive signal 402, the energy of an acoustic beam transmitted from each individual transducer element (or each group of transducer elements) may be effectively adjusted to provide the intended level defined in the treatment plan. FIGS. 4B and 4C depict how the duty cycle of the driver signal may be increased to 75% or reduced to 25%, respectively, using PWM.

Figure 5:
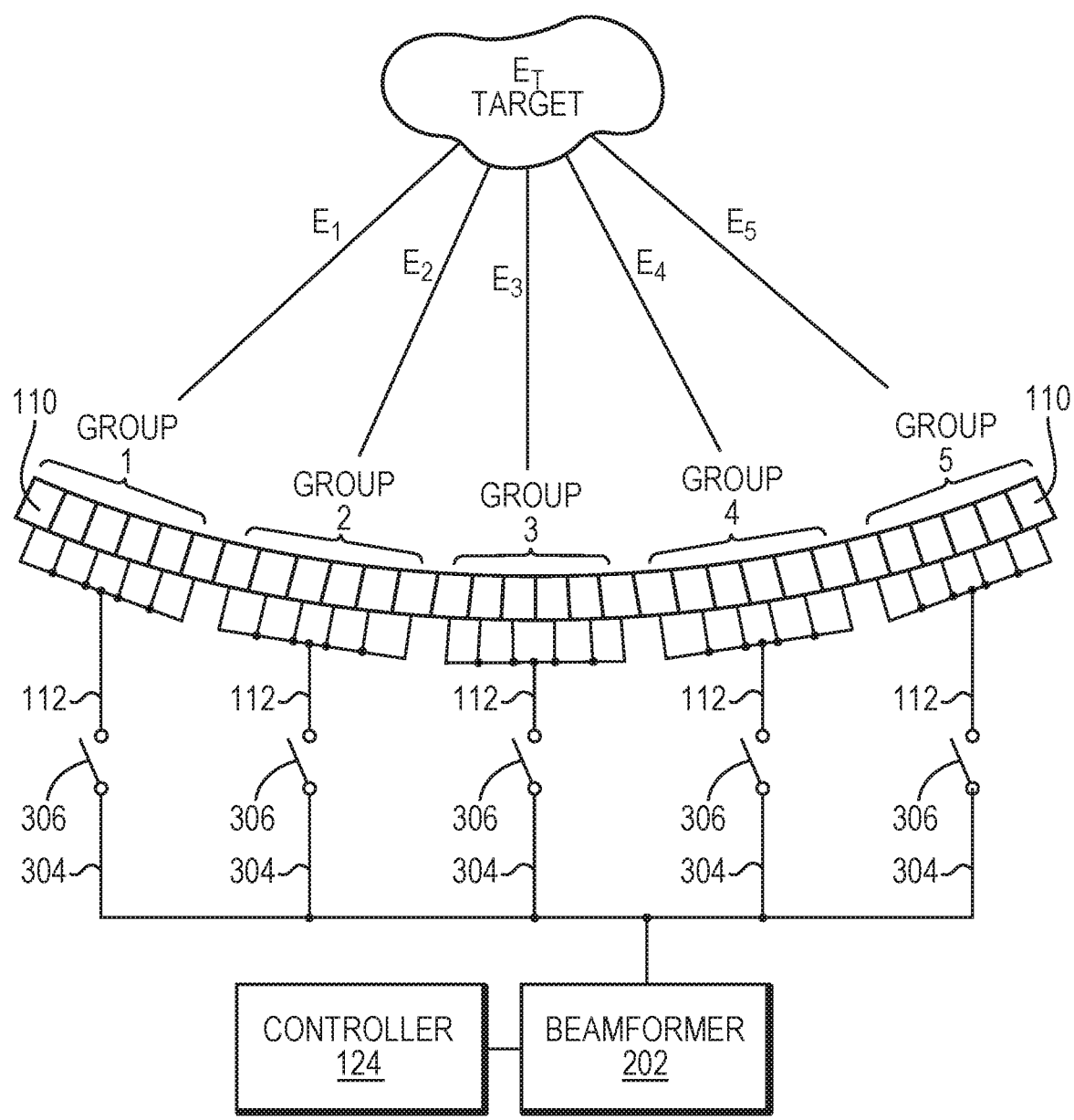
FIG. 5 depicts a transducer-array configuration in accordance with various embodiments.

During ultrasound operation, various groups of the transducer elements 110 may be sequentially activated in round-robin fashion to apply and maintain the target average energy level at the target region. For example, referring to FIG. 5, the transducer elements may be grouped into groups 1-5; groups 1-5 may be sequentially activated and deactivated via the switches 306 of the cross-point matrix 302 for delivering a desired amount of acoustic energy to the target region. In some embodiments, the controller 124 adjusts the duty cycle of the drive pulse associated with each group of transducer elements based on a corresponding emitted acoustic energy reaching the target region and the target average energy level set forth in the treatment plan. Generally, higher target average energy levels correspond to higher duty cycles, and the greater the degree of attenuation (i.e., the lower the transmitted energy reaching the target region), the higher will be the required duty cycle. For example, if the target average energy level is $E_T$ and the energy generated from group 1 elements and reaching the target region 104 is $E_1$, the duty cycle of the group 1 elements may be determined by (or proportional to) the ratio of $E_T/E_1$. Duty cycles for other groups may be similarly determined. Accordingly, when the groups of transducer elements are sequentially activated with their determined corresponding duty cycles, each of them generates substantially the same average energy level $E_T$ at the target region; this ensures that the target average level is maintained during the entire ultrasound procedure. The proper initial duty cycle may be computed mathematically, as just described, or determined (or refined) empirically by measuring the temperature effects of various duty cycles using thermometry without undue experimentation.

In one embodiment, more than one group of transducer elements is substantially simultaneously activated to deliver acoustic beams to the target region 104. This embodiment may be preferable when the energy levels of the acoustic beams are significantly attenuated by the intervening tissue. In this situation, the energy level at the target region from a group of elements may be too small to generate the target average energy level even with a full duty cycle (i.e., 100%). Thus, it is desirable to simultaneously activate more than one group of the transducer elements such that the summed energy level at the target region can reach the desired target average level.

Figure 6:
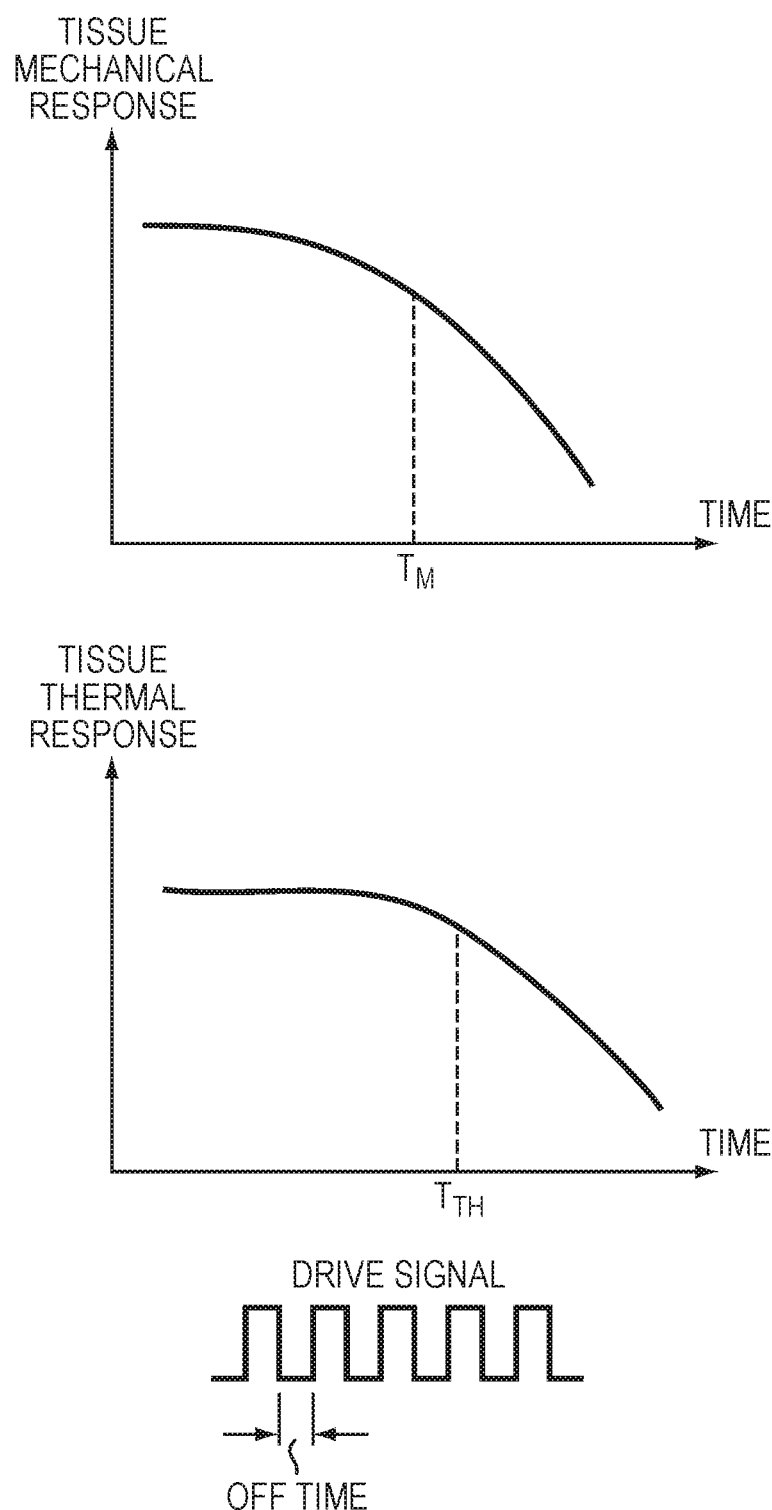
FIG. 6 schematically depicts tissue responses to deactivation of the transducer elements in accordance with various embodiments.

In various embodiments, the duty cycles of the drive signals associated with the groups of the transducer elements are determined based on the time constant of the targeted tissue. This is because although the target tissue may mechanically and thermally respond to the applied acoustic pulses, such tissue responses are typically not instantaneous to the applied beam energy. For example, during the "off time" of the drive signals (i.e., when the transducer elements are deactivated), the tissue may gradually relax as depicted in FIG. 6. A mechanical time constant, $T_M$, and a thermal time constant, $T_{TH}$, represent the relaxation behavior. Therefore, to ensure that the tissue responses are not significantly impacted by deactivation of the transducer elements, the off time of a drive signal and/or between two drive signals is preferably smaller than the (collective) time constant of the targeted tissue. Generally, the off time may be a few times smaller than $T_M$ and $T_{TH}$ to sufficiently ensure that the tissue responses have not been significantly affected between two acoustic pulses. In some embodiments, the off time is smaller than $T_M$ and $T_{TH}$ by at least one order of magnitude.

Generally, the mechanical and thermal responses of the tissue highly depend on the type of the tissue. Accordingly, in one embodiment, the time constants of various tissue types are acquired empirically prior to treatment; this information is stored as a lookup table in a database and may be retrieved when determining the duty cycles of signals for driving the transducer elements. In another embodiment, the time constants of various tissue types are acquired during treatment. For example, the transducer array may first deliver an acoustic pulse to the target region 104, and based on the tissue responses monitored using the imager 308, the mechanical and thermal time constants associated with the target tissue can be determined.

The mechanical and/or thermal response of the target tissue, however, may be nonlinear resulting from cumulative thermal energy. Thus, in various embodiments, the imager 308 monitors the tissue response in real time during treatment and provides the monitored information as feedback to the controller. If the mechanical and/or thermal time constant varies significantly during treatment, the controller 124 may responsively adjust the duty cycle(s) of the drive signal(s) to the transducer elements (or groups of transducer elements) to ensure that activation and deactivation of the elements does not result in clinically significant effects on the target tissue.

In one implementation, based on the monitored tissue response time constant(s), the controller may calculate a maximal off time (which determines the duty cycle) of the transducer elements 110 while still achieving the desired treatment outcome. This approach may increase the transducer lifetime (by reducing its operation time) while still achieving the desired treatment plan.

In various embodiments, the imager 308 (e.g., an MRI apparatus) simultaneously monitors a temperature of the target during the ultrasound procedure. This is particularly useful in MR-guided thermal therapy (e.g., MRgFUS treatment), where the temperature of a treatment area should be continuously monitored in order to assess the progress of treatment and correct for local differences in heat conduction and energy absorption to verify that the targeted tissue was treated and avoid damage to tissues surrounding the treatment area. The monitoring (e.g., measurement and/or mapping) of temperature with MR imaging is generally referred to as MR thermometry or MR thermal imaging.

Among various methods available for MR thermometry, the proton resonance frequency (PRF) shift method is often the method of choice due to its excellent linearity with respect to temperature change, near-independence from tissue type, and temperature map acquisition with high spatial and temporal resolution. The PRF shift method is based on the phenomenon that the MR resonance frequency of protons in water molecules changes linearly with temperature (with a constant of proportionality that, advantageously, is relatively constant between tissue types). Since the frequency change with temperature is small, only −0.01 ppm/° C. for bulk water and approximately −0.0096 to −0.013 ppm/° C. in tissue, the PRF shift is typically detected with a phase-sensitive imaging method in which the imaging is performed twice: first to acquire a baseline PRF phase image prior to a temperature change and then to acquire a second phase image during or after the temperature change—i.e., a treatment image—thereby capturing a small phase change that is proportional to the change in temperature. A map of temperature changes may then be computed from the (reconstructed, i.e., real-space) images by determining, on a pixel-by-pixel basis, phase differences between the baseline image and the treatment image, and converting the phase differences into temperature differences based on the PRF temperature dependence while taking into account imaging parameters such as the strength of the magnetic field and echo time (TE) (e.g., of a gradient-recalled echo).

If the temperature distribution in the imaged area at the time of acquisition of the baseline image is known, the temperature-difference map can be added to that baseline temperature in order to obtain the absolute temperature distribution corresponding to the treatment image. In some embodiments, the baseline temperature is simply uniform body temperature throughout the imaging region. More complicated baseline temperature distributions are, in some embodiments, determined prior to treatment by direct temperature-measurements in various locations in combination with interpolation and/or extrapolation based on a mathematical fit (e.g., a smooth, polynomial fit).

In various embodiments, the monitored temperature is provided to the controller 124, which, in response, adjusts the duty cycles of the transducer elements (or groups of transducer elements) such that a desired temperature level set forth in the treatment plan can be achieved. For example, when the monitored temperature in the target region is lower than the target temperature level set forth in the treatment plan, the controller 124 may increase the duty cycles of the signals driving the transducer elements so as to increase the total energy transmitted to the target region; this thereby increases the temperature. Alternatively, the amplitude of the drive signals associated with all elements (or all groups of elements) may be increased substantially simultaneously to increase the energy transmitted to the target region. Similarly, if the monitored temperature in the target region is higher than the target temperature level, the controller 124 may reduce the duty cycles and/or amplitudes to prevent overheating. Adjustment of the duty cycles and/or amplitudes may be iteratively performed until the monitored temperature level substantially matches the target temperature level.

Figure 7A:
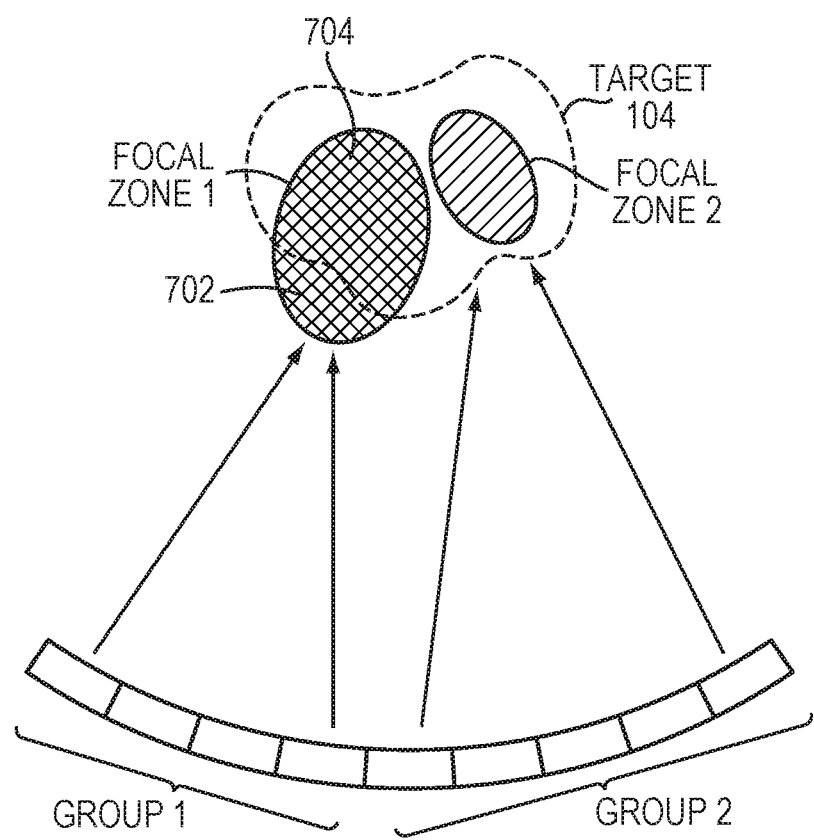
FIGS. 7A and 7B depict multiple focal zones generated by multiple groups of transducer elements in accordance with various embodiments.

Sequentially activating the groups of transducer elements as described above may also advantageously avoid damage to the tissue surrounding the target region. Referring to FIG. 7A, in some embodiments, each group of the transducer elements generates a focal zone at the target region. Ideally, each generated focal zone matches precisely to the area of the target region. But in practice, the acoustic beams may be distorted due to inhomogeneity of the intervening tissue; as a result, one or more focal zones may be distorted and extend beyond the boundary of the target region to its surrounding tissue. For example, as depicted in FIG. 7A, groups 1 and 2 of the transducer elements may generate focal zones 1 and 2, respectively. While the entire focal zone 2 is within the boundary of the target region, a portion 702 of the focal zone 1 covers the tissue surrounding the target. If attempts to focus energy at the target region are performed merely by activating the group 1 transducer elements, excessive heat may be delivered to the surround tissue in region 702 and cause damage thereto. However, when the groups 1 and 2 of the transducer elements are sequentially activated and deactivated in accordance with their determined duty cycles as described above, thermal energy delivered to the region 702 may be less excessive and avoid damage thereto. In various embodiments, the temperature of the surrounding tissue during the ultrasound procedure is monitored using the imager 308. If the temperature is above a safe threshold and may therefore cause damage, the controller 124 may completely deactivate the group 1 transducer elements or at least reduce the duty cycle of the group 1 transducer elements.

Figure 7B:
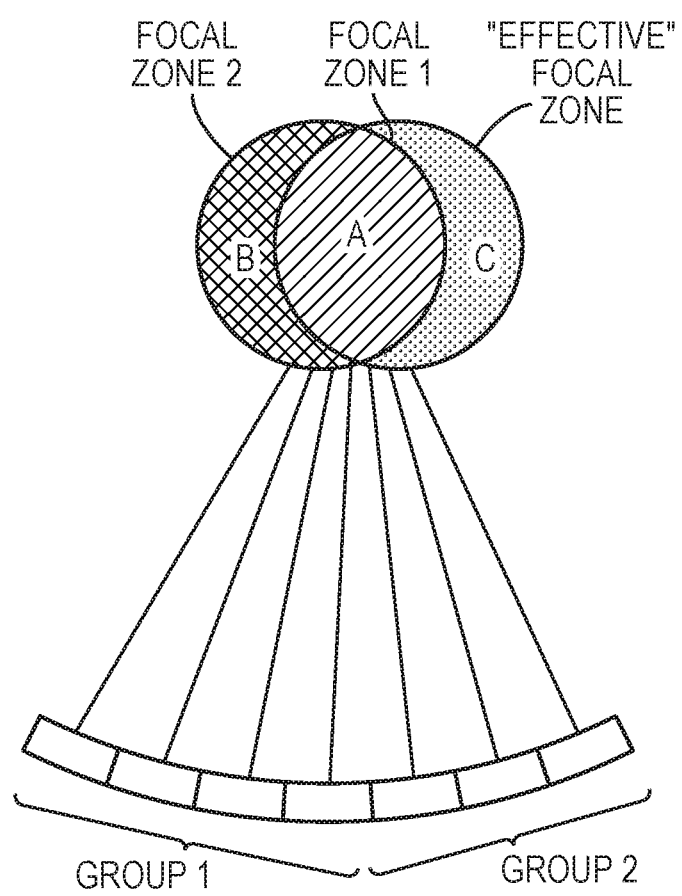

In addition, the imager 308 may be further configured to monitor the location and/or profile of the focus generated by the entire transducer array. Based on the monitored data, the controller 124 may operate the cross-point switch matrix 302 to adjust the duty cycles of the groups of the transducer elements so as to direct the focal zone to the desired target location and/or reduce profile distortion of the focal zone. For example, referring to FIG. 7B, group 1 of the transducer elements may generate focal zone 1 including regions A and B, and group 2 of the transducer elements may generate focal zone 2 including regions A and C. Thus, the "effective" focal zone generated by the elements in groups 1 and 2 includes regions A, B, and C. Because region A is the overlap of focal zones 1 and 2, region A may have a higher energy level compared with regions B and C. Assuming that focal zone 1 at region B results from beam distortion and is thus unwanted, upon detection of this focal distortion, the controller 124 may reduce the duty cycle of group 1 transducer elements so as to reduce the distortion. In response to this adjustment, the controller 124 may optionally increase the duty cycle of group 2 transducer elements to compensate for energy reduced particular in region A. Accordingly, this approach allows the focal zone of the transducer array to be effectively "shaped" so as to minimize (or at least reduce) undesired effects resulting from beam distortions caused by the intervening tissue.

Figure 8:
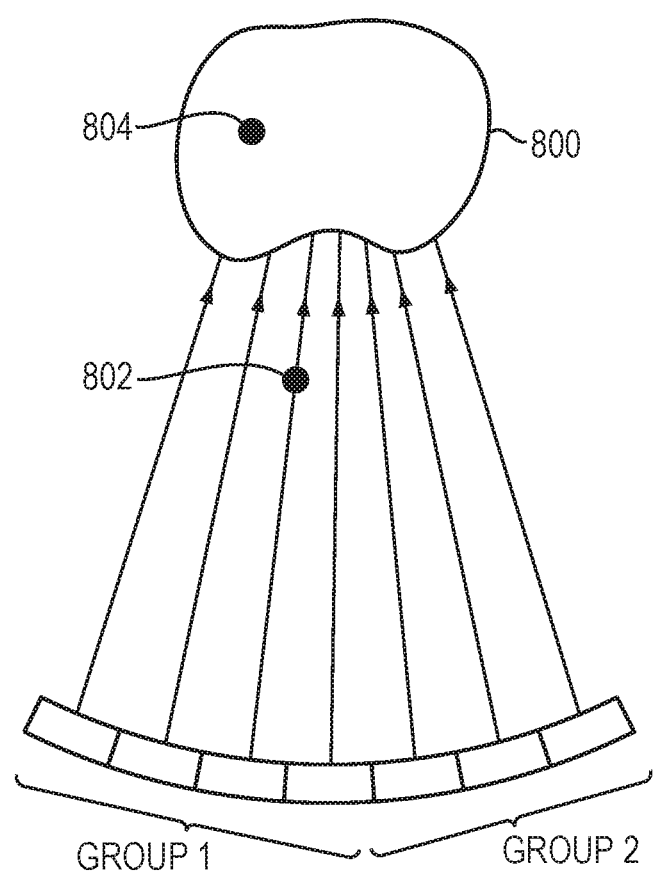
FIG. 8 schematically illustrates hot spots generated in the focal and/or non-focal zones in accordance with various embodiments.

In some embodiments, inhomogeneity of the intervening tissues may create one or more hot spots of an inhomogeneous temperature distribution at locations other than the intended focal zone. Such hot spots may lead to undesired heating, pain for the patient, and/or possibly necrosis of non-targeted tissue; even within the target tissue, hot spots can be problematic by, for example, causing tissue necrosis outside the target region. In addition, in cases where each transducer is made up of a finite number of elements, if phasing is performed in discrete phase steps as described above, this may also contribute to the creation of secondary hot spots. FIG. 8 depicts an exemplary situation where activation of group 1 of the transducer elements generates a focal zone 800 at the target region as well as an undesired hot spot 802 on the beam path and an undesired hot spot 804 within the focal zone, while activation of group 2 of the transducer elements generates a focused beam at the same focal zone 800 but without undesired hot spots. In various embodiments, the imager 308 is configured to monitor generation and locations of the hot spots. When undesired hot spots are detected, the imager 308 communicates their locations to the controller 124. In response, the controller reduces the duty cycle and/or amplitude of all elements of the group(s) of transducer elements that generate the hot spots. Accordingly, effects of the hot spots may be reduced as they do not persist for a sufficient amount of time to cause a clinically adverse effect on target or intervening tissue. This approach may thus effectively improve uniformity of the resulting temperature distribution in the target region as well as preventing damage to the surrounding tissue due to hot spots.

Reducing the duty cycle of the transducer elements, however, comes with a tradeoff of reducing the thermal energy at the target region as well, and thereby compromising the treatment effects. To avoid this issue, in some embodiments, after the duty cycle is reduced to a predetermined threshold (e.g., defined as a percentage of the duty cycle that generates focusing peak intensity), the amplitude(s) of the transducer element group(s) that generate the hot spots may be increased to compensate for the decrease of thermal energy at the target region.

Figure 9:
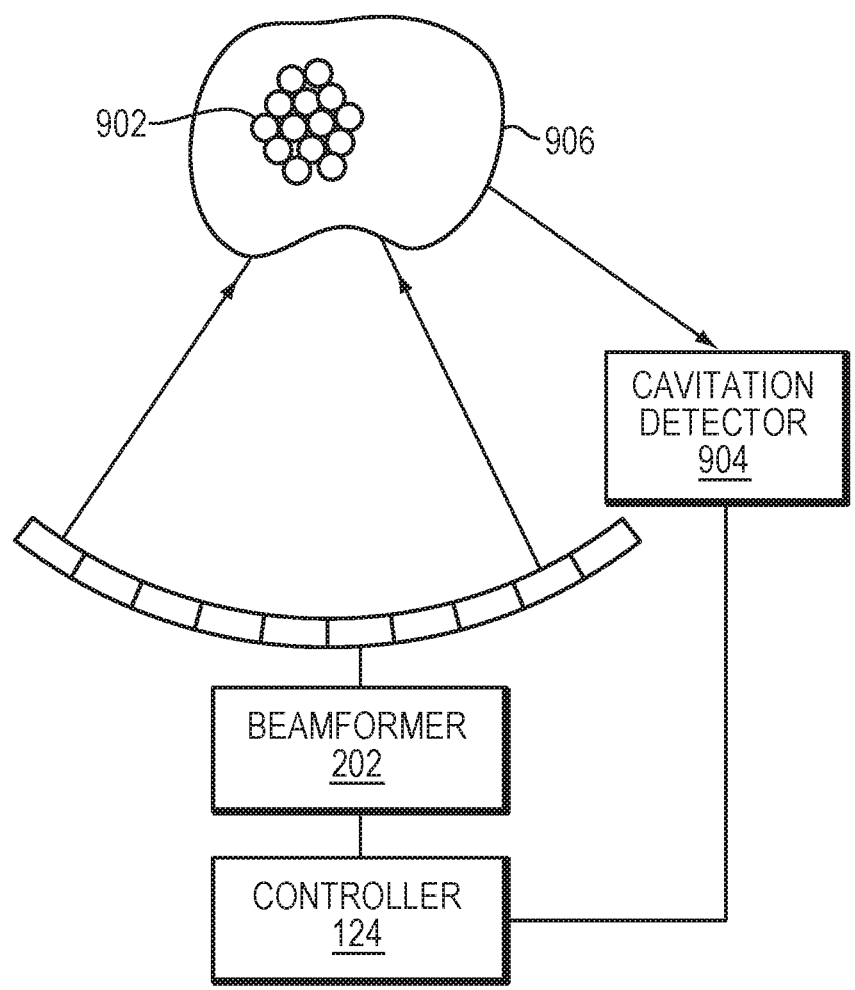
FIG. 9 schematically depicts microbubbles generated in the focal zone in accordance with various embodiments.

Referring to FIG. 9, during a focused ultrasound procedure, small gas bubbles (or "microbubbles") 902 may be generated in the liquid contained in the target tissue, e.g., due to the stress resulting from negative pressure produced by the propagating ultrasonic waves and/or from when the heated liquid ruptures and is filled with gas/vapor. In stable cavitation, microbubbles are steaming while their volumes remain constant or, in some cases, expand and contract with the acoustic pressure rarefaction and compression over several cycles; such action can result in a sheer force and dilation and contraction of the tissue in the vicinity. In inertial cavitation, the microbubbles can expand to several factors greater than their equilibrium radius and subsequently collapse due to the inertia of the surrounding tissue. In both cases, the consequent disruption of the target tissue may assist ablation thereof.

An uncontrolled microbubble cavitation, however, may result in undesired damage to and around the target tissue. Accordingly, there is a preferred range of the cavitation amount (or cavitation dose) that may promote ablation of the target tissue while minimizing the undesired effects resulting from the cavitation. To ensure the degree of cavitation is in the preferred range, in various embodiments, a cavitation detector 904, coupled to the controller, is implemented for detecting cavitation at the focal zone 906 and/or outside the focal zone during the ultrasound procedure. The cavitation detector 904 measures transmitted or reflected acoustic waves from the microbubbles 902, and subsequently provides the signals it receives to the controller 124 for determining the amount of cavitation occurring in the focal zone 906. Based on the determined cavitation amount, the controller may responsively operate the cross-point switch matrix 302 to activate or deactivate one or more of the transducer element groups and/or adjust the duty cycle(s) thereof such that the degree of cavitation in the focal zone is within the preferred range. For example, if the measured cavitation amount is above the preferred range and may cause undesired damage to the target tissue or its surrounding tissue, the controller 124 may deactivate one or more groups of the transducer elements and/or reduce the duty cycle(s) of the group(s) to reduce the peak pressure at the focal zone; as a result, the cavitation amount may be reduced. If, however, a larger amount of cavitation than measured is desired in order to assist tissue ablation, the controller 124 may activate one or more groups of the transducer elements and/or increase the duty cycle(s) of the group(s); consequently, a larger peak pressure is generated at the focal zone to induce more microbubble cavitation.

In various embodiments, a portion of the transducer array acts as the cavitation detector. For example, the controller 124 may assign one or more groups of the transducer elements to measure the acoustic signals transmitted or reflected from the microbubbles 902. Again, the measured signals are transmitted to the controller 124 for determining the amount of cavitation in the focal zone 906 and operations of the transducer elements may be adjusted to create a desired cavitation amount. This embodiment advantageously obviates the need of implementing a separate cavitation detector.

Accordingly, embodiments of the present invention provide approaches allowing the controller 124 to operate the transducer elements for generating a focal zone at the target location with desired focusing properties. This is achieved by implementing a cross-point switch matrix between the transducer elements and the beamformer. By selectively activating and deactivating switches associated with one or more transducer elements (or groups of transducer elements) and/or adjusting the duty cycle(s) thereof, a treatment plan (e.g., a target average intensity level, a target average energy level and/or a target temperature level) can be achieved. Because the switches may be simply manipulated using PWM, this implementation does not require excessive system complexity and cost. In addition, an imager (e.g., an MRI apparatus) and/or a cavitation detector may be employed to monitor a treatment parameter (e.g., a temperature or a cavitation amount) in the target and/or non-target region; the monitored parameter may then be provided as feedback to the controller for adjusting operation of the transducer elements in order to achieve the treatment plan.

In general, functionality for performing activation and deactivation of the switches in the cross-point matrix, adjusting the duty cycles of the transducer elements, measuring a temperature in the target and non-target region and/or detecting a cavitation amount in the focal zone, as described above, whether integrated within a controller of the imager, and/or an ultrasound system, or provided by a separate external controller, may be structured in one or more modules implemented in hardware, software, or a combination of both. For embodiments in which the functions are provided as one or more software programs, the programs may be written in any of a number of high level languages such as FORTRAN, PASCAL, JAVA, C, C++, C#, BASIC, various scripting languages, and/or HTML. Additionally, the software can be implemented in an assembly language directed to the microprocessor resident on a target computer (e.g., the controller); for example, the software may be implemented in Intel 80x86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

In addition, the term "controller" used herein broadly includes all necessary hardware components and/or software modules utilized to perform any functionality as described above; the controller may include multiple hardware components and/or software modules and the functionality can be spread among different components and/or modules.

Certain embodiments of the present invention are described above. It is, however, expressly noted that the present invention is not limited to those embodiments; rather, additions and modifications to what is expressly described herein are also included within the scope of the invention.

What is claimed is:

1. A system for delivering ultrasound energy to an internal anatomical target, the system comprising:
   an ultrasound transducer comprising a plurality of transducer elements collectively operable as a phased array;
   a plurality of driver circuits, each of the driver circuits being connected to at least one of the transducer elements;
   a plurality of phase circuits;
   a switch matrix selectably coupling the driver circuits with the phase circuits; and
   a controller configured for (i) receiving as input at least one of a target average intensity level to be applied to the target or an energy level to be applied to the target, (ii) identifying a plurality of sets of the transducer elements, each of the sets corresponding to a plurality of the transducer elements for focusing and/or shaping, as a phased array, ultrasound energy at the target across tissue intervening between the target and the ultrasound transducer, and (iii) sequentially operating the transducer-element sets to apply and maintain the target average energy level at the target,
   wherein the controller sequentially operates each of the transducer element sets in accordance with a pulse-width modulation pattern having a duty cycle determined based at least in part, for a currently operated transducer element set, on the ultrasound energy generated from the currently operated transducer element set and reaching the target so as to achieve and maintain at least one of (i) the target average intensity level or (ii) the energy level at the target in accordance with an estimated time constant of the target tissue across all of the transducer element sets during their sequential operation.

2. The system of claim 1 where the phase circuits deliver signals having a discrete number of fixed phase shifts, and the controller is further configured to apply one of the fixed phase shifts to one of the transducer elements or to one of the transducer element sets.

3. The system of claim 2, wherein the controller is further configured to adjust the fixed phase shifts based on one of the shaping of the ultrasound energy or a location of the target.

4. The system of claim 1, further comprising a magnetic resonance (MR) unit for monitoring a temperature of the target, wherein the controller is configured to adjust the duty cycle in response to the monitored temperature.

5. The system of claim 4, wherein the controller is further configured to responsively operate the switch matrix to energize or ground selected ones of the transducer elements of each of the sets so as to reduce temperature inhomogeneities in at least one of an ultrasound beam path zone or the target detected by the MR monitoring.

6. The system of claim 4, wherein the MR unit is further configured to monitor a location and profile of the focus, the controller being further configured to responsively operate the switch matrix to energize or ground selected ones of the transducer elements of each of the sets so as to reduce profile distortion of the focus.

7. The system of claim 1, wherein the driver circuits are greater in number than the phase circuits, the controller selectively connecting each of the phase circuits to a plurality of the driver circuits.

8. The system of claim 1, wherein the switch matrix is a crosspoint switch matrix.

9. The system of claim 1, further comprising a cavitation detector for detecting cavitation at the focus, the controller being further configured to responsively operate the switch matrix to energize or ground selected ones of the transducer elements of each of the sets so as to reduce peak pressure at the focus in the presence of detected cavitation.

10. The system of claim 9, wherein the cavitation detector is coupled to the controller, the controller being further configured to (i) responsively operate the switch matrix to energize or ground selected ones of the transducer elements of each of the sets and (ii) facilitate pulse width modulation of signals driving the plurality of the sets of the transducer elements so as to achieve a cavitation effect in a predefined range.

11. The system of claim 1, wherein at least one transducer element is shared between at least two sets of the transducer elements.

12. The system of claim 1, wherein the controller is further configured to simultaneously operate more than one set of the transducer elements.

13. The system of claim 1 wherein the switch matrix is configured to couple the driver circuits to at least one of the phase circuits, an electrical ground, or a voltage source having a fixed voltage.

14. The system of claim 1, wherein the controller is further configured to operate each of the transducer element sets to produce a point focus, a line focus or a ring-shaped focus at the target.

15. The system of claim 1 wherein the controller is further configured to operate the transducer elements to generate multiple foci at the target.

16. The system of claim 1, wherein the controller is further configured to sequentially operate the transducer-element sets in round-robin fashion.

17. The system of claim 1, wherein the target average intensity level is a spatial average intensity level.

18. The system of claim 1, wherein the target average intensity level is a temporal average intensity level.

19. A method for delivering ultrasound energy to an internal anatomical target utilizing an ultrasound transducer comprising a plurality of transducer elements collectively operable as a phased array, a plurality of driver circuits each connected to at least one of the transducer elements, a plurality of phase circuits, and a switch matrix selectably coupling the driver circuits with the phase circuits, the method comprising:
  receiving as input at least one of a target average intensity level to be applied to the target or an energy level to be applied to the target,
  identifying a plurality of sets of transducer elements, each of the sets corresponding to a plurality of the transducer elements for shaping and/or focusing, as a phased array, ultrasound energy at the target across tissue intervening between the target and the ultrasound transducer,
  sequentially operating the transducer-element sets to apply and maintain the target average energy level at the target,
    wherein each of the transducer element sets is sequentially operated in accordance with a pulse-width modulation pattern having a duty cycle determined based at least in part, for a currently operated transducer element set, on the ultrasound energy generated from the currently operated transducer element set and reaching the target so as to achieve and maintain at least one of (i) the target average intensity level or (ii) the energy level at the target in accordance with a time constant of the target tissue across all of the transducer element sets during their sequential operation.

20. The method of claim 19, further comprising monitoring a temperature of the target and adjusting the duty cycle in response to the monitored temperature.

21. The method of claim 19, further comprising monitoring temperature inhomogeneities in at least one of an ultrasound beam path zone or the target and responsively operating the switch matrix to energize or ground selected ones of the transducer elements of each of the sets so as to reduce the temperature inhomogeneities.

22. The method of claim 19, further comprising monitoring a location and profile of the focus, and responsively operating the switch matrix to energize or ground selected ones of the transducer elements of each of the sets so as to reduce profile distortion of the focus.

23. The method of claim 19, wherein the driver circuits are greater in number than the phase circuits, the method further comprising selectively connecting each of the phase circuits to a plurality of the driver circuits.

24. The method of claim 19, further comprising detecting cavitation at the focus and responsively operating the switch matrix to energize or ground selected ones of the transducer elements of each of the sets so as to reduce peak pressure at the focus in the presence of detected cavitation.

25. The method of claim 19, further comprising:
  detecting cavitation at the focus;
  responsively operating the switch matrix to energize or ground selected ones of the transducer elements of each of the sets; and
  facilitating pulse width modulation of signals driving the plurality of the sets of the transducer elements so as to achieve a cavitation effect in a predefined range.

26. The method of claim 19, further comprising simultaneously operating more than one set of the transducer elements.

27. The method of claim 19, wherein the phase circuits deliver signals having a discrete number of fixed phase shifts, the method further comprising applying one of the fixed phase shifts to one of the transducer elements or one of the transducer element sets.

28. The method of claim 27, further comprising adjusting the fixed phase shifts applied to the one of the transducer elements or the one of the transducer element sets based on one of the shaping of the ultrasound energy or a location of the target.

29. The method of claim 19, further comprising operating each of the transducer element sets for producing a point focus, a line focus or a ring-shaped focus at the target.

30. The method of claim 19, further comprising sequentially operating the transducer-element sets in round-robin fashion.

31. The method of claim 19, further comprising operating the transducer elements to generate multiple foci at the target.

32. The method of claim 19, wherein the target average intensity level is a spatial average intensity level.

33. The method of claim 19, wherein the target average intensity level is a temporal average intensity level.

\* \* \* \* \*